United States Patent [19]

Kahn

[11] 4,204,329
[45] May 27, 1980

[54] RUBBER DAM HOLDER FOR USE DURING ENDODONTIC THERAPY

[75] Inventor: Henry Kahn, 1724 Grand Bahama West, Palm Springs, Calif. 92262

[73] Assignee: Henry Kahn, Palm Springs, Calif.

[21] Appl. No.: 951,346

[22] Filed: Oct. 16, 1978

[51] Int. Cl.² ............................................. A61C 5/12
[52] U.S. Cl. .................................................... 433/136
[58] Field of Search ................. 32/34, 35; 128/12, 13, 128/14

[56] References Cited

U.S. PATENT DOCUMENTS

| | | | |
|---|---|---|---|
| 604,890 | 5/1898 | Seeger | 32/35 |
| 682,308 | 9/1901 | Young | 32/35 |

OTHER PUBLICATIONS

Dam-E-Z-Ray,, Apr. 1968, Rinn Corporation, 1212, Abbott Drive, Elgin Illinois 60120.

Primary Examiner—Robert Peshock

[57] ABSTRACT

The present invention comprises a frame to hold a rubber dam for use during dental surgery. The frame is substantially U-shaped in configuration and convex so as to generally follow the contours of the face. A hinge is positioned in the center of the bottom of the U so that the side frames may individually pivot toward each other or may be brought together. Detent means are positioned on the external surface of the bottom of the frame so that when the vertical members of the frame are pivoted to each other they may be secured together in this folded position. Barbed means are provided on the frame to hold the rubber dam when the frame is in use. In use, the rubber dam is secured to the barbed means on the frame and the frame is placed over the patient's face. An opening is made in the rubber dam and the rubber dam is then clamped to or about the tooth which is to be treated. If it is necessary to have access to the interior of the patient's mouth, either side of the frame may be pivoted to the other or the two frames may be brought together substantially perpendicular to the patient's face. The convex shape of the frame coupled with the dam clamp within the mouth of the patient is sufficient to hold the frame in place during operative procedures, including X-rays if necessary.

8 Claims, 3 Drawing Figures

RUBBER DAM HOLDER FOR USE DURING ENDODONTIC THERAPY

FIELD OF INVENTION

This invention relates generally to dental surgery, and more particularly to a rubber dam holder for use during endodontic therapy.

BACKGROUND AND SUMMARY OF THE INVENTION

During endodontic therapy it is customary to maintain the field aseptic by a dam consisting of a flexible web of rubber stretched in place over a frame lying against or adjacent the patient's face. A hole is formed in the dam and a clasp is secured to the dam. The clasp in turn is clamped to the tooth being operated on.

In the course of such therapy it may be necessary to take one or more roentgenograms. The dam must then be temporarily moved aside to allow placement of the roentgenogram in the oral cavity. The dam should be moved aside in such manner that risk of contamination of the field and possible distortion of the roentgenogram are minimized. Furthermore, the procedure should be carried out with the least loss of time and discomfort to the patient.

It is an object of the present invention to provide a holder for a flexible dam for the purpose stated, said holder comprising sections movably connected together in a manner such that a part of the dam, e.g. one-half, may be quickly and easily displaced from the mouth-covering position when it is desired to take a roentgenogram, while retaining the other part of the dam in sterile-maintaining position. However, if the position of the film holder with respect to the dam holder is such that partial overlap occurs, the holder may be fabricated of a plastics composition which is transparent to X-rays.

It is a further object of the present invention to provide a dam holder for the stated purpose in which the dam remains secured to the frame when the latter is moved to an inactive position. This not only materially reduces the possibility of contaminating the sterile field during taking of roentgenograms, but facilitates manipulation of the frame.

It is a still further object of the invention to provide a holder in the form of a frame that is relatively small in size and compact as compared to frames heretofore used, and wherein the taking of roentgenograms is greatly facilitated with minimum discomfort to the patient or loss of time for the operator.

In accordance with the principles of the invention, a frame is desirably fabricated in the form of a U of molded plastics composition which is transparent to X-rays. The legs or sides of the frame carry a number of arrow-shaped pins, also desirably transparent to X-rays, by means of which the dam is secured to the frame. The pointed head of the pins permits the dam to be readily attached to the frame while preventing inadvertent slippage. The bight of the frame is divided into two symmetrical halves hingedly connected together at the mid-plane thereof. The hinge axis is substantially parallel to the sides of the frame in order that, when the dam is in operating position on the frame and clamped to the tooth being treated, either the left or right hand part of the frame can be swung about the hinge axis to allow sufficient access to the oral cavity for placement of a roentgenogram.

In another embodiment the frame is molded in one piece with the two halves pivotally joined by a so-called "living hinge". In this molded embodiment the cost of the device is considerably reduced, is lighter in weight, and there are no mechanically articulated connections which may jam or break. Furthermore, the inclusion of a resilient snap latch, the parts of which are integrally molded with the two halves of the frame enables the frame to be readily positioned with one leg folded back when X-rays are being taken.

DESCRIPTION OF THE PREFERRED EMBODIMENT

Figure 1:
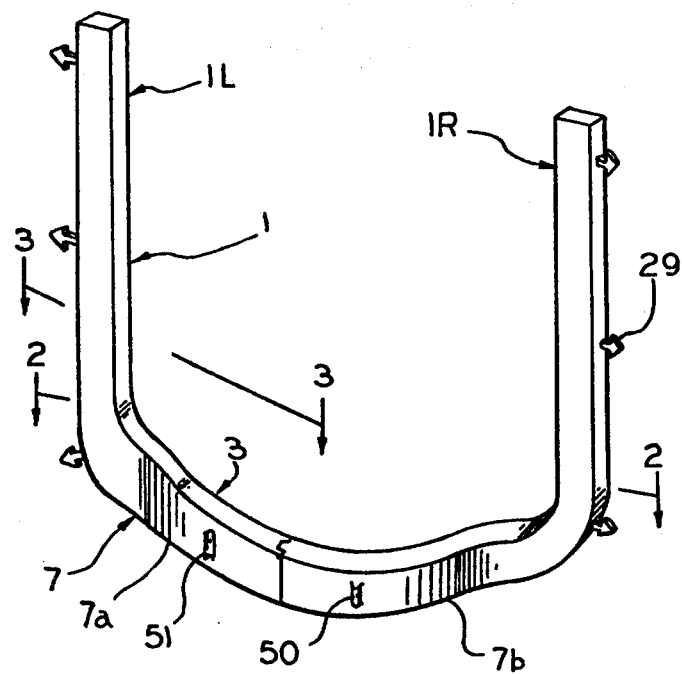
FIG. 1 is a perspective view from the front, of a device embodying the invention, shown in open position.
Figure 2:
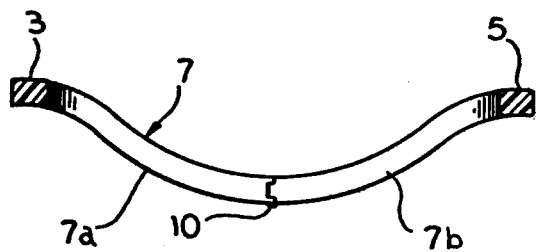
FIG. 2 is a cross-section taken on the line 2—2 of FIG. 1.

Referring to the drawing, the numeral 1 designates a U-shaped frame of reasonably rigid plastics material preferably of resilient character but shape-retaining, e.g., polyethylene, polypropylene, nylon, or the like to withstand fracture under the conditions of use. Desirably the frame comprises two symmetrical halves 1R and 1L; the legs of the U are joined by a bight 7 connecting the two halves 1R and 1L of the frame. The legs are substantially parallel. The halves are disposed in a common plane, but the bight 7 is preferably bowed outwardly of this plane better to conform the frame substantially to the outwardly convex configuration of a patient's face. The two halves 1R and 1L are hinged together on a vertical axis, as will be described, to allow the oral cavity to be exposed for the purpose described above.

The hinging of the two halves 1R and 1L is preferably effected by means of a "living hinge". This is a term of art describing a hinged interconnection between two members molded in one piece of a pliant plastics composition in such a way that the members are capable of repeated flexure about a hinge axis without cracking or breaking. By utilizing a hinged connection of this nature, metal parts and resultant spurious roentgenograms are avoided. In the present case the hinged connection permits access to the oral cavity by folding either or both halves out of the principal plane of the frame. The desired flexure is obtained by means of a thin ligament 10 between the halves 7a and 7b. It will be understood that the dimensions of the ligament will be so related to the pliancy of the material as to permit repeated flexure without giving rise to significant over-stretching and possible set. Desirably the two halves 7a and 7b are provided with a respective tongue 7c and mating groove 7d adapted to supplement support provided by the ligament 10. It will be understood that the material utilized for the device will be capable of being sterilized.

Figure 3:
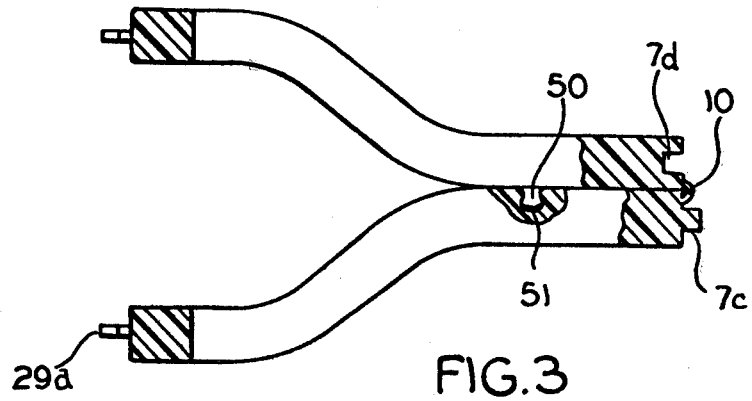
FIG. 3 is a cross-section taken on the line 3—3 of FIG. 1.

In order to supplement the location of the two halves 7a and 7b, when folded, a snap-type detent may be provided (FIG. 3) comprising a female element 50 and a male element 51 formed in the halves 7a and 7b respectively. In the example, the element 50 consists of an essentially tubular conformation having a longitudinal opening and the element 51 is in the form of a cylinder, so constructed and arranged as to snap into the element 50 when the two halves 7a and 7b are swung to closed position (FIG. 3). No tools are required since the parts are so configured as to be snapped or unsnapped by opposition of the thumb and finger. By employing cylindrical male and female members for the detent, the two halves 7(a) and 7(b) snap into each other over a considerably greater span than a conventional "dot" snap fastener.

To anchor the rubber sheet (not shown) in stretched condition on the frame, there is provided a plurality of pins 29a in the form of arrowheads or other barb-like projections adapted to pierce the sheet and remain engaged therewith by reason of the points piercing the rubber sheet when this latter is forced over the pins, whereafter the arrow-head will engage reliably behind the sheet.

During treatment the frame is in the rigid or expanded position shown in FIG. 1, in which the frame sides flank the patient's oral cavity and the dam overlies the cavity. After sterilization of the field the dam functions to prevent the patient's tongue and/or saliva from contaminating the field. When a roentgenogram is to be exposed the frame with the roller dam held stretched thereon is placed with the dam across the oral cavity. In this position access to the outer position of the oral cavity is readily attainable, access to the patient's mouth, viz, positioning of the roentgenogram, the dam meanwhile remaining in secured relation with the tooth. As is conventional, the patient may hold the roentgenogram with this fingertip. During the procedure the field remains sterile and the pins 29 preserve the position of the dam relatively to the frame. After the roentgenogram is exposed the frame is folded back to its extended position.

I claim:

1. A frame for supporting an elastomeric web exterior of the oral cavity of a patient during endodontic therapy, said frame comprising two counter-facing L-shaped parts hinged together to define a U-shaped frame, the hinge being positioned in the center of the base of said U-shaped frame, the pivotal axis of said hinge being essentially perpendicular to the planes of the occlusal surfaces of the patient's teeth, the base of the U-shape frame having a convex configuration to place each of the upright members of said frame substantially parallel to the respective cheeks of the patient, a plurality of hook-like elements on the frame to be engaged by the web, the said two parts of the base of said U-shape frame carrying respective male and female detent elements adapted to engage each other when said frame is folded about said hinge axis.

2. A frame for detachably mounting a rubber sheet to constitute a dam isolating the oral cavity from a tooth upon which dental work is being performed, said frame comprising two symmetrical L-shaped halves of convex configuration disposed in a common plane, each half adapted to be positioned adjacent the respective cheek of a patient, the respective foot of each L-shaped half being mutually aligned and meeting substantially in said plane, hinge means having a vertical hinge axis integral with said feet and connecting the two halves, said hinge comprising a pliable strap joined at its ends to the respective ends of said feet.

3. The combination in accordance with claim 2 further characterized by a plurality of barbs integrated with and outstanding from the two halves, each barb included a shank and a sharpened head to facilitate puncturing of the dam when impaling the same on the barbs.

4. The combination in accordance with claim 2 wherein the feet lie in a curved plane forming an arched and inwardly concave configuration.

5. The combination in accordance with claim 2 further characterized by means to register the two halves when the frame is folded about the hinge axis, said registering means comprising male and female detent elements on respective ones of the two feet.

6. In combination, a U-shaped frame to support a sheet rubber dam in stretched relation therewith, comprising two opposing symmetrical L-shaped halves each on one side of a pivotal axis connecting the respective ends of the feet of said halves, said pivotal axis comprising hinge means having a vertical pivotal axis common to said halves to enable the two halves to be pivoted between a position with the halves fully open to cover the oral cavity with the dam and a position with at least one of said halves pivoted about said vertical axis to enable access to the oral cavity, each half comprising material which is transparent to X-rays, the hinge means comprising a pliable ligament formed integrally with, and extending between, the adjacent, aligned ends of the respective foot part of each half, each of said halves carrying a plurality of means to impale said rubber dam, each foot of said halves carrying means to engage each other when said halves are pivoted about said vertical hinge access.

7. A frame for supporting a sheet rubber dam as used, for example, in endodontics techniques to isolate the operative site from the oral cavity, and frame comprising at least three members disposed generally like a U, two of the members being the legs of the U and one member being like the bight of the U, a plurality of barbs spaced apart on and secured to the members, said barbs adapted to hold the dam in stretched condition over the patient's oral cavity, said one bight member comprising two parts meeting substantially at a midplane bisecting the U, hinge means connecting said members for rotation with respect to each other whereby each half of the frame may be swung with respect to the other to expose the associated portions of the oral cavity, snap-type detent means intermediate the bight parts adapted to engage when the said parts are rotated to align the detent means and forced into engaged relation to preserve access to the oral cavity and a pliable ligament connecting the two bight parts to constitute the hinge means.

8. The combination in accordance with claim 7 wherein said members, barbs, hinge means comprise material transparent to X-rays.

* * * * *